(12) United States Patent
Sacripante et al.

(10) Patent No.: US 9,427,392 B2
(45) Date of Patent: Aug. 30, 2016

(54) NAIL POLISH COMPOSITIONS

(71) Applicant: XEROX CORPORATION, Norwalk, CT (US)

(72) Inventors: Guerino G. Sacripante, Oakville (CA); Adela Goredema, Mississauga (CA); Naveen Chopra, Oakville (CA); Ke Zhou, Oakville (CA); Marcel P. Breton, Mississauga (CA)

(73) Assignee: XEROX CORPORATION, Norwalk, CT (US)

( * ) Notice: Subject to any disclaimer, the term of this patent is extended or adjusted under 35 U.S.C. 154(b) by 124 days.

(21) Appl. No.: 14/050,212

(22) Filed: Oct. 9, 2013

(65) Prior Publication Data

US 2015/0098971 A1 Apr. 9, 2015

(51) Int. Cl.
*A61Q 3/02* (2006.01)
*A61K 8/85* (2006.01)
*A61K 8/06* (2006.01)

(52) U.S. Cl.
CPC . *A61K 8/85* (2013.01); *A61K 8/06* (2013.01); *A61Q 3/02* (2013.01)

(58) Field of Classification Search
None
See application file for complete search history.

(56) References Cited

U.S. PATENT DOCUMENTS

| | | | |
|---|---|---|---|
| 5,348,832 A | 9/1994 | Sacripante et al. | |
| 5,538,717 A * | 7/1996 | La Poterie | 424/61 |
| 5,747,018 A | 5/1998 | Valenty | |
| 5,925,336 A * | 7/1999 | Garber et al. | 424/61 |
| 6,384,108 B1 | 5/2002 | Breton et al. | |
| 6,432,601 B1 * | 8/2002 | Foucher | G03G 9/08755 430/109.4 |
| 6,664,015 B1 * | 12/2003 | Sacripante | C08G 63/6886 430/108.1 |
| 6,818,723 B2 | 11/2004 | Sacripante | |
| 2003/0236379 A1 * | 12/2003 | Sacripante | 528/10 |
| 2005/0152714 A1 * | 7/2005 | Lansdown | 399/103 |
| 2007/0189995 A1 * | 8/2007 | Weber et al. | 424/61 |

* cited by examiner

*Primary Examiner* — Brian Gulledge
(74) *Attorney, Agent, or Firm* — Pillsbury Winthrop Shaw Pittman LLP

(57) ABSTRACT

Personal care products for maintaining fingernail and toenail appearance. In particular, nail polish compositions that have a formulation that is both safer and more environmentally-friendly to use. The present nail polish compositions comprise anionic polyester resins such as sodio-sulfonated polyesters and sodio-sulfonated co-polyester-co-polysiloxane copolymers as base resin vehicles.

11 Claims, No Drawings

NAIL POLISH COMPOSITIONS

TECHNICAL FIELD

The presently disclosed embodiments are generally directed to nail polish compositions. These compositions are odor-free and aqueous-based to provide a nail polish composition that are both safer and more environmentally-friendly to use. In embodiments, the present compositions include, but are not limited to, color enamels, nail varnishes, nail lacquers, clear base coats, topcoats, and nail hardeners.

BACKGROUND

Generally, conventional nail polish compositions have a base composition of organic solvents containing a resin or primary film-forming agent, an aryl-sulfamide formaldehyde resin, or an alkyd resin, and a plasticizing agent. The resins are often ones including nitrocellulose, polyacrylates, styrene-acrylates, polyurethanes, polyester urethanes, and the like. These resins all have unwanted residual monomers or isocyanate residual and are used in combination with organic solvents to enable film formation.

In particular, nitrocellulose provides good adhesion of the compositions to nails upon application, and is the preferred conventional film-forming agent for use in nail polish compositions. Nitrocellulose, however, is highly flammable, and thus, may pose safety hazards during the manufacturing process for nail polish compositions that require the use of nitrocellulose. Additionally, the solvents used to dissolve nitrocellulose such as toluene, isopropanol, ethyl acetate, butyl acetate or mixtures thereof, are also flammable and have unpleasant odor. As such, alternatives to nitrocellulose, which provide good adhesion to nails but which avoid the negative issues associated with nitrocellulose, are sought to either reduce the amount of nitrocellulose used in the composition or entirely replace the nitrocellulose in the composition.

Other common components of nail polish such as formaldehyde, toluene and phthalate help provide a product that is long-lasting and fast drying. These components provide the nail polish with desirable attributes: toluene allows dilution of the resin and fast drying time of the polish, formaldehyde provides cross linking with keratin and offers good cohesion, and phthalate increases homogeneity of the film. However, the toxicity of these compounds is pushing cosmetic companies to identify alternative technologies while keeping the original attributes.

It has also been discovered that the use of aqueous-based nail polish compositions may help avoid the problems associated with conventional, organic solvent-based compositions. Aqueous compositions avoid much of the problem associated with non-aqueous compositions, such as, smell, toxicity to environment and damage to the nail. The problem with aqueous-based nail polish compositions, however, is that such compositions are generally slow to dry. Thus, such compositions would benefit from faster setting film-forming agents.

Therefore, there exists a need for new film-forming agents to be used in aqueous nail polish compositions which may reduce or replace the amount of organic solvents and nitrocellulose needed—providing a safer and more environmentally-friendly composition. Moreover, the resulting nail polish composition is preferably free of formaldehyde, toluene and phthalate. In aqueous-based compositions, such film-forming agents should be faster setting to help provide a nail polish composition that is not slow drying and still maintain good adhesion and glossiness.

BRIEF SUMMARY

According to embodiments illustrated herein, there is provided a nail polish composition that avoids the problems associated with conventional nail polish compositions, as discussed above.

An embodiment may include an aqueous-based nail polish composition, comprising: an emulsion of a sulfonated polyester resin in water; and an optional pigment; and an optional thickening agent.

In another embodiment, there is provided an aqueous-based nail polish composition, comprising: an emulsion of a sulfonated polyester resin in water; and an optional pigment, wherein the sulfonated polyester resin is selected from the group consisting of a sodio-sulfonated polyester resin, a sodio-sulfonated co-polyester-co-polysiloxane resin and mixtures thereof.

In yet further embodiments, there is provided an aqueous-based nail polish composition, comprising: an emulsion of a branched sulfonated polyester resin in water; and an optional pigment, wherein the aqueous-based nail polish composition is odorless and has a viscosity at 25° C. of from about 5 to about 5,000 cps.

Finally, in embodiments, there is provided a method of preparing an aqueous-based nail polish composition, comprising: adding a sulfonated polyester resin to water; emulsifying the-sulfonated polyester resin in water to obtain an emulsification; and adding an optional pigment to the emulsification to obtain an aqueous-based nail polish composition.

DETAILED DESCRIPTION

In the following description, it is understood that other embodiments may be used and structural and operational changes may be made without departing from the scope of the present disclosure.

In the present embodiments, there are provided nail polish compositions that comprise particular anionic polyester resins as the film-forming agent. The resins include highly viscous ones such as sulfonated polyester (SPE). Particular embodiments include sodio-sulfonated polyesters and sodio-sulfonated co-polyester-co-polysiloxanes.

These resins are odor-less, unlike styrene-acrylates, and non-toxic unlike polyurethanes (derived from isocyanates). Moreover, the sodio-sulfonated polyesters and sodio-sulfonated co-polyester-co-polysiloxane dissipate (or emulsify) readily in water (at temperatures greater than 85° C.) to form emulsions with particle sizes in the desired range of from about 10 to about 300 nm. The resulting emulsions form robust films after drying.

Fingernails and toenails are made of a tough protein called keratin, which is a family of fibrous structural proteins that are typically inert and water-insoluble. A sclera-protein occurs as an aggregate due to hydrophobic side chains that protrude from the molecule. The proteins comprise of peptide sequence such as a collagen helix, which feature cross-links between chains (e.g., cys-cys disulfide bonds between keratin chains). Overall, these surfaces tend to be cationic due to amide bonds of the peptide sequence. The anionic properties of the polyester resins of the present embodiments bind easily to the nail (cationic proteins).

The present nail polish compositions provide a number of attributes, including being long-lasting (remains on nails for a minimum of 5 days, and in some embodiments, a minimum of 7 days), having the ability to form a homogeneous film on nails, compatible with inorganic pigments, providing shiny, glossy coat, fast-drying (for example, drying within 80 seconds), being odorless, being safe for application to human nails and being easy to apply. In addition, because the present compositions avoid many of the organic solvents used in conventional nail polish compositions, the present compositions are much more gentler on the nails and nail components.

In embodiments, the nail polish composition comprises a sulfonated polyesters of the formula or as essentially represented by the formula:

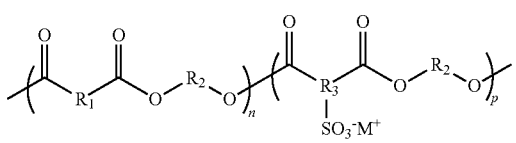

wherein M is a Hydrogen or Alkali metal such as lithium or sodium, and $R_1$ and $R_3$ is independently selected from the group consisting of aryl and alkyl; $R_2$ is independently selected from the group consisting of alkyl and oxyalkylene, and wherein n and p represent random segments of the polymer; and are each about 10 to about 100,000 units. In embodiments, $R_1$ is selected from the group consisting of terephthalyl, isophthalyl, phthalyl, xylyl, 1,4-cyclohexyl, 1,3-cyclohexyl, 1,2-cyclohexyl, 1,4-naphthyl, 1,7-naphthyl, 1,6-naphthyl, 1,3 naphthyl, 1,2-naphthyl, 1,8-naphthyl, and biphenyl. In embodiments, $R_2$ is methyl, ethyl, propyl, butyl, pentyl, hexyl, heptyl, octyl, nonyl, decyl, undecyl, dodecyl, stearyl, lauryl, neopentyl, 1,2-propyl, 1,2-butyl, 1,3-butyl, 2-pentyl, 2,2-dimethylpropyl, and an oxyalkylene of diethyleneoxide, dipropyleneoxide, triethyleneoxide, and mixture thereof. In another embodiment, the nail polish composition comprises a sulfonated co-polyesters-copolysiloxane of the formula or as essentially represented by the formula:

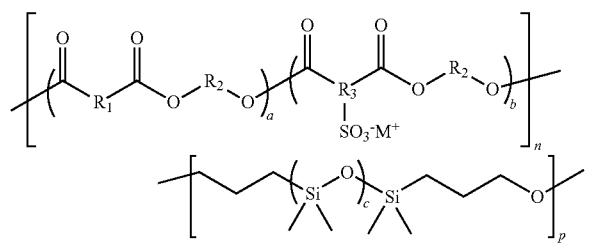

wherein M is a hydrogen or alkali metal such as lithium or sodium, and $R_1$ and $R_3$ is independently selected from the group consisting of aryl and alkyl; $R_2$ is independently selected from the group consisting of alkyl and oxyalkylene, and wherein a, b, c, n and p represent random segments of the polymer; and are each about 10 to about 100,000 units In embodiments, $R_1$ is selected from the group consisting of terephthalyl, isophthalyl, phthalyl, xylyl, 1,4-cyclohexyl, 1,3-cyclohexyl, 1,2-cyclohexyl, 1,4-naphthyl, 1,7-naphthyl, 1,6-naphthyl, 1,3 naphthyl, 1,2-naphthyl, 1,8-naphthyl, and biphenyl. In embodiments, $R_2$ and $R_3$ is methyl, ethyl, propyl, butyl, pentyl, hexyl, heptyl, octyl, nonyl, decyl, undecyl, dodecyl, stearyl, lauryl, neopentyl, 1,2-propyl, 1,2-butyl, 1,3-butyl, 2-pentyl, 2,2-dimethylpropyl, and an oxyalkylene of diethyleneoxide, dipropyleneoxide, triethyleneoxide, and mixture thereof.

In general embodiments, the sulfonated polyester is derived from at least one dicarboxylic acid, at least one diol and at least one component of a sulfonated ion attached to a dicarboxylic acid or diol component. In particular embodiments, the sulfonated polyester is derived from dimethyl terephthalate, dimethyl-5-sulfo-isophthalate sodium salt, 1,2-propanediol and diethylene glycol. In further embodiment, the sulfonated co-polyesters-copolysiloxane is derived from at least one dicarboxylic acid, at least one diol and at least one component of a sulfonated ion attached to a dicarboxylic acid or diol component. In particular embodiments, the sulfonated polyester is derived from dimethyl terephthalate, dimethyl-5-sulfo-isophthalate sodium salt, 1,2-propanediol and diethylene glycol, and a bis-carbinol terminated polydimethylsiloxane such as Bis-3-propyl-polydimethylsiloxane available from Gelest Inc, and of the formula;

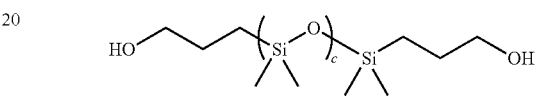

wherein c represents the number of repeat units and is an integer of from about 10 to about 100,000.

In further embodiments, the dicarboxylic acid or diester is selected from the group consisting of terephthalic acid, phthalic acid, isophthalic acid, fumaric acid, maleic acid, succinic acid, itaconic acid, succinic anhydride, succinic anhydride, dodecylsuccinic acid, dodecylsuccinic anhydride, glutaric acid, glutaric anhydride, adipic acid, pimelic acid, suberic acid, azelic acid, dodecanediacid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and mixtures thereof. In such embodiments, the diol is selected from the group consisting of ethanediol, 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis(hyroxyethyl)-bisphenol A, bis(2-hyroxypropyl)-bisphenol A, 1,4-cyclohexanedimethanol, 1,3-cyclohexanedimethanol, xylenedimethanol, cyclohexanediol, diethylene glycol, bis(2-hydroxyethyl) oxide, dipropylene glycol, dibutylene, and mixtures thereof. In embodiments, polyfunctional acid and alcohols can also be utilized to provide with branched polyester compositions, and wherein such polyfunctional acids are comprised of trimellitic anhydride, trimellitic acid, glycerol, trmethylol-prpane mictures thereof and the like.

In the present embodiments, the sulfonated component is comprised of hydrogen, ammonium, lithium, sodium, potassium, cesium, berylium, magnesium, calcium, barium, strontium, iron, copper, vanadium, chromium, manganese, and cobalt of the sulfonated difunctional monomer dimethyl-5-sulfo-isophthalate, dialkyl-5-sulfo-isophthalate-4-sulfo-1,8-naphthalic anhydride, 4-sulfo-phthalic acid, dimethyl-4-sulfo-phthalate, dialkyl-4-sulfo-phthalate, 4-sulfophenyl-3,5-dicarbomethoxybenzene, 6-sulfo-2-naphthyl-3,5-dicarbomethoxybenzene, sulfo-terephthalic acid, dimethyl-sulfo-terephthalate, 5-sulfo-isophthalic acid, dialkyl-sulfo-terephthalate, sulfoethanediol, 2-sulfopropanediol, 2-sulfobutanediol, 3-sulfopentanediol, 2-sulfohexanediol, 3-sulfo-2-methylpentanediol, 2-sulfo-3,3-dimethylpentanediol, sulfo-p-hydroxybenzoic acid, N,N-bis(2- hydroxyethyl)-2-amino ethane sulfonate, or mixtures thereof. In more particular embodiments, the sulfonated polyester is comprised of M+ ions of random copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly-(propylene-diethylene-5-sulfoisophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), copoly(ethoxylated bisphenol-A-maleate)copoly(ethoxylated bisphenol-A-5-sulfo-isophthalate), and mixtures thereof. In a specific embodiment, the sulfonated component is dimethyl 5-sulfo-isophthalate sodium salt.

Sulfonated polyesters and sulfonated co-polyester-co-polysiloxane were previously explored in toner applications, such as for example, in U.S. Pat. Nos. 5,348,832, 6,384,108, and 6,818,723, which are hereby incorporated by reference in their entireties, and found to provide excellent fusion to papers. The incorporation of such resins into nail polish compositions resulted in many unexpected benefits.

The disclosed anionic polyester resins are emulsified in water to produce an emulsion. The emulsions produced have particle sizes in the desired range of from about 10 to about 500 nm, or from about 10 to about 300 nm, or from about 10 to about 250 nm. In embodiments, the anionic polyester resin is present in the composition in an amount of from about 1 to about 80 percent, or from about 1 to about 35 percent, or from about 1 to about 15 percent by weight of the total weight of the nail polish composition. In embodiments, the water is present in the composition in an amount of from about 1 to about 95 percent, or from about 10 to about 80 percent, or from about 25 to about 75 percent by weight of the total weight of the composition.

The resulting nail polish composition has a viscosity at 25° C. of from about 1 to about 10,000 cps, or of from about 1 to about 1,000 cps. or of from about 1 to about 100 cps. The viscosity was measured on a RFS3 controlled strain Rheometer (from TA Instruments, Inc.) equipped with a Peltier heating plate and using a 25 mm parallel plate at 25 degrees centigrade. The composition dries in less than 80 seconds, or from about 10 to about 80 seconds, or from about 10 to about 50 seconds. The composition provides a glossiness of from about 20 to about 120, or from about 60 to about 90 gloss units as measured by the Gardner Gloss Metering Unit. The composition also provides a satisfactory adhesion as measured by the Hofman Scratch-hardness tester. The nail polish composition of the present embodiments resulted in similar scratch and hardness to conventional nail polish compositions.

The nail polish compositions according to the present embodiments may also contain at least one thickening agent in a proportion of from 0.01% to 5%, and preferably between 0.1% and 1%, by weight of the total weight of the polish. Thickening agents proving suitable for the aqueous nail polish formulation include cellulose and the derivatives thereof, such as carboxymethylcellulose and hydroxyethylcellulose, silicates, clays such as laponite, synthetic polymers such as acrylic or associative polyurethane-type polymers, and natural gums, such as carrageenan or xanthane gum. A thickening agent chosen from among hydroxyethylcellulose, laponite, and the associative polyurethanes is preferably selected.

Other finely ground (having a particle size not to exceed 50 microns) water-soluble inorganic powders may be used, such as boron nitride, smectite clays, silica, zinc oxide, iron oxides, calcium and magnesium carbonates, and lakes. Because lakes are available commercially in various colors as FDA-approved products for nail polishes (such as the various aluminum, zirconium, barium, strontium, potassium and calcium lakes sold by chemical companies such as Universal Foods Corporation of Plainfield, N.J., and Seltzer Chemicals Inc. of Carlsbad, Calif.), they are particularly useful as thickening agents for colored nail polishes.

Finely ground, water-insoluble organic powders are also suitable thickening agents for sulfonate-containing polymers dispersed in water. These agents comprise microcrystalline cellulose, polyaromatic amides (sold by The DuPont Company under the trademark "Kevlar"), polyethylene, nylon, and polyester, used either alone or in combination with the finely ground inorganic material described above When the nail polish compositions according to the present embodiments are colored, they then contain at least one organic or inorganic pigment in a proportion of between 0.01% and 5% by weight, and preferably between 0.5% and 2% by weight of the total weight of the polish. Such pigments may include colors such as red, yellow, magenta, black, green, orange, pink, blue, purple, brown and mixtures thereof. For example, organic pigments include D and C Red, Nos. 10, 11, 12 and 13, D and C Red No. 7, D and C Red Nos. 5 and 6, D and C Red Nos, 30 and 34, lacquers such as D and C Yellow No. 5 and D and C Red No. 2, or guanine. The group of inorganic pigments comprises titanium dioxide, bismuth oxychloride, brown iron oxide, and the red iron oxides. The nail polish composition may also be clear, for example, free or substantially free of pigments to provide a clear coat over the nail.

Moreover, it is possible to adjust the spreadability of the polishes by using water-soluble fluorinated surfactants, including perfluoroalkyl compounds sold under the trade names FORAFAC 1179, FORAFAC 1098, FORAFAC 1157, ZONYL-FSN (DuPont Company), ZONYL FSC (DuPont Company), ZONYL FSP (DuPont Company), ZONYL UR (DuPont Company), FLUORAD FC 129 (3M Company), FLUORAD FC 135 (3M Company), FLUORAD FC 170C (3M Company), FLUORAD FC 120 (3M Company), FLUORAD FC 143 (3M Company), and the like and mixtures thereof. The proportion of water-soluble fluorinated surfactants may be between 0.01 and 1% by weight, and preferably between 0.05 and 0.2% by weight, of the total weight of the nail polish.

The nail polish compositions according to the present embodiments may further contain at least one additive selected from among a wetting agent, a dispersing agent, an anti-foaming agent, a sunscreen, a preservative, a drying-acceleration agent, a wax, a silicone, or a mixture thereof.

As discussed above, the final composition can bind to the cationic proteins on human nail surfaces. Data shows that the present composition is equivalent to the conventional nail polishes in film forming, adhesion and gloss.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter. The resins used in these examples are defined below:

Example 1

Black Nail Polish Derived from Sodio Sulfonated Polyester Resin and Carbon Black Sodio-sulfonated polyester resin, as prepared and described in U.S. Pat. No. 5,348,832, which is hereby incorporated by reference in its entirety, was heated in water at 85-90° C. to provide with an emulsion of about 35% solids in water. In a 50 mL beaker, the emulsion was added (5.68 g) followed by carbon black 300 (4.35 g, available from Cabot Corp.). The mixture was stirred with a magnetic stir bar at room temperature for about 10 minutes to give a homogenous formulation.

Example 2

Black Nail Polish Derived from Sodio Sulfonated Co-Polyester Co-poly-Siloxane Resin and Carbon Black An aqueous emulsion of sodio sulfonated co-polyester co-poly-siloxane resin, as prepared and described in U.S. Pat. No. 6,818,723, which is hereby incorporated by reference in its entirety, was heated in water at 85-90° C. to provide with an emulsion of about 21% solids in water. In a 50 mL beaker, the emulsion was added (6.83 g) followed by carbon black 300 3.17 g, available from Cabot Corp.). The mixture was stirred with a magnetic stir bar at room temperature for about 10 minutes to give a homogenous formulation.

Example 3

Magenta Nail Polish Derived from Sodio Sulfonated Co-Polyester Co-Poly-Siloxane Resin and Magenta Pigment The nail polish composition for this example was prepared in the same way as Example 2 except that magenta pigment was used in place of carbon black as shown in Table 1 below.

Examples 4-5

Red Nail Polish Derived from Sodio Sulfonated Co-Polyester Co-Poly-Siloxane Resin Nail polish compositions of these examples were prepared in the same way as Example 2 except that red pigment was used in place of carbon black as shown in Table 1 below.

TABLE 1

| | Example 1 | Example 2 | Example 3 | Example 4 | Example 5 |
|---|---|---|---|---|---|
| Sodio-Sulfonated polyester resin BSPE (33.95% solids) | 19.30 | | | | |
| Sodio Sulfonated co-Polyester co-poly-siloxane Resin (20.60% solids) | | 14.06 | 14.06 | 14.06 | 24.06 |
| Cabo-jet 300 (carbon Black) | 6.47 | 4.71 | | | |
| Cabo-jet 480 V (magenta) | | | 4.71 | | |
| Sun Chemical MCM-059-SJ (Red) | | | | 4.71 | 4.71 |
| Water | 74.24 | 81.23 | 81.23 | 81.23 | 71.23 |
| Total | 100.00 | 100.00 | 100.00 | 100 | 100.00 |
| Viscosity 25° C. (cps) | | 2.32 | 2.11 | 2.14 | 7.46 |
| Drying Time (seconds) | <80 | <80 | <80 | <80 | |
| Image Robustness (done visually and compared to commercial nail polish) | Poor | Excellent | Excellent | Excellent | |

Nail Polish Composition Performance

The polish obtained by the above compositions spread easily on the nail and allowed to dry. Drying time was assessed by time required for all the water to evaporate leaving robust film that could not be easily removed by rubbing with a Q-tip. Image robustness was assessed by removing the nail Polish by rubbing with a Q-tip.

Water-resistance of the polish obtained was analyzed by applying a 300 µm film on a glass plate, then by immersing it for one hour while stirring in cold or hot (45° C.) water, with or without detergent. No discoloration was then observed, nor were any tearing or dissolution of the film over time noted. The polish obtained thus had excellent water-resistance, in particular to hot water, even in the presence of a detergent.

The composition provides comparable glossiness, as measured by the Gardner Gloss Metering Unit, and comparable scratch and hardness, as measured by the Hofman Scratch-hardness tester, to conventional nail polish compositions.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An aqueous-based nail polish composition, comprising:
    an emulsion of a sulfonated polyester resin in water, wherein the sulfonated polyester resin is present in the composition in an amount of from about 1 to about 15 percent by weight of the total weight of the composition;
    an optional pigment; and
    a thickening agent in the amount of from 0.01% to 5% by weight of the total weight of the nail polish composition;
    wherein the sulfonated polyester resin comprises a sulfonated co-polyesters-copolysiloxane having the following formula:

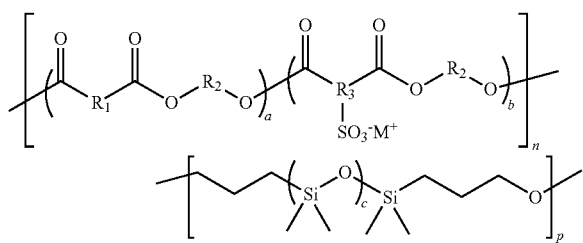

wherein M is a hydrogen or an alkali metal; $R_1$ and $R_3$ is independently selected from the group consisting of aryl and alkyl; $R_2$ is independently selected from the group consisting of alkyl and oxyalkylene; and a, b, c, n and p are each independently about 10 to about 100,000;

wherein the aqueous-based nail polish composition having a viscosity at 25° C. of from about 5 to about 5,000 cps, the aqueous-based nail polish composition having a drying time of less than 80 seconds, and a glossiness of from about 60 to about 100 gloss units, wherein the glossiness is measured using a Gardner Gloss Metering Unit.

2. The aqueous-based nail polish composition of claim 1, wherein the optional pigment is selected from the group consisting of red, yellow, magenta, black, green, orange, pink, blue, purple, brown and mixtures thereof.

3. The aqueous-based nail polish composition of claim 1, wherein the emulsion has a particle size of from about 10 to about 100 nm.

4. The aqueous-based nail polish composition of claim 1, wherein the optional pigment is present in the composition in an amount of from about 1 to about 15 percent by weight of the total weight of the composition.

5. The aqueous-based nail polish composition of claim 1, wherein the water is present in the composition in an amount of from about 10 to about 95 percent by weight of the total weight of the composition.

6. The aqueous-based nail polish composition of claim 1 being odorless.

7. The aqueous-based nail polish composition of claim 1, wherein the optional pigment is an organic pigment selected from the group consisting of red, yellow, magenta, black, green, orange, pink, blue, purple, brown and mixtures thereof or an inorganic pigment selected from the group consisting of titanium dioxide, bismuth oxychloride, brown iron oxide, red iron oxides, and mixtures thereof.

8. The aqueous-based nail polish composition of claim 1 further including an additive selected from the group consisting of a wetting agent, a dispersing agent, an antifoaming agent, a sunscreen, a preservative, a drying-acceleration agent, a wax, a silicon, and mixtures thereof.

9. An aqueous-based nail polish composition, comprising:
an emulsion of a branched sulfonated polyester resin in water, wherein the sulfonated polyester resin is present in the composition in an amount of from about 1 to about 15 percent by weight of the total weight of the composition;
an optional pigment; and
a thickening agent in the amount of from 0.01% to 5% by weight of the total weight of the nail polish composition;
wherein the sulfonated polyester resin comprises a sulfonated co-polyesters-copolysiloxane having the following formula:

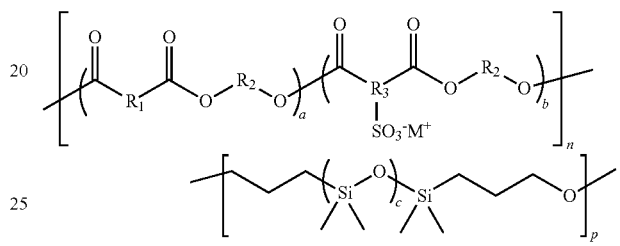

wherein M is a hydrogen or an alkali metal; $R_1$ and $R_3$ is independently selected from the group consisting of aryl and alkyl; $R_2$ is independently selected from the group consisting of alkyl and oxyalkylene; and a, b, c, n and p are each independently about 10 to about 100,000;

further wherein the aqueous-based nail polish composition is odorless and has a viscosity at 25° C. of from about 5 to about 5,000 cps, and a glossiness of from about 60 to about 100 gloss units, wherein the glossiness is measured using a Gardner Gloss Metering Unit.

10. A method of preparing the aqueous-based nail polish composition according to claim 1, comprising:
adding the sulfonated polyester resin to water;
emulsifying the-sulfonated polyester resin in water to obtain an emulsification; and
adding an optional pigment to the emulsification to obtain an aqueous-based nail polish composition.

11. The method of claim 10 further including storing the aqueous-based nail polish composition in a container.

* * * * *